United States Patent
Gross (10) Patent No.: US 9,370,660 B2
(45) Date of Patent: Jun. 21, 2016

(54) INDEPENDENTLY-CONTROLLED BIDIRECTIONAL NERVE STIMULATION

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 129 days.

(21) Appl. No.: 14/226,723

(22) Filed: Mar. 26, 2014

(65) Prior Publication Data

US 2014/0296940 A1     Oct. 2, 2014

Related U.S. Application Data (60) Provisional application No. 61/806,448, filed on Mar. 29, 2013.

(51) Int. Cl.
     *A61N 1/36*          (2006.01)
     *A61N 1/05*          (2006.01)

(52) U.S. Cl.
     CPC ........ *A61N 1/36135* (2013.01); *A61N 1/36157* (2013.01); *A61N 1/0556* (2013.01); *A61N 1/36053* (2013.01); *A61N 1/36064* (2013.01); *A61N 1/36067* (2013.01); *A61N 1/36171* (2013.01)

(58) Field of Classification Search
     CPC ........... A61N 1/36135; A61N 1/36175; A61N 1/36064; A61N 1/36157; A61N 1/36053; A61N 1/36067; A61N 1/0556
See application file for complete search history.

(56) References Cited

U.S. PATENT DOCUMENTS

| | | |
|---|---|---|
| 3,411,507 A | 11/1968 | Wingrove |
| 3,941,136 A | 3/1976 | Bucalo |
| 4,019,518 A | 4/1977 | Maurer et al. |
| 4,161,952 A | 7/1979 | Kinney et al. |

(Continued)

FOREIGN PATENT DOCUMENTS

| | | |
|---|---|---|
| EP | 0688577 A1 | 12/1995 |
| EP | 0831954 A1 | 4/1998 |

(Continued)

OTHER PUBLICATIONS

Office Action issued Aug. 6, 2009, in connection with U.S. Appl. No. 10/205,475, filed Jul. 24, 2002.

(Continued)

*Primary Examiner* — Catherine Voorhees
(74) *Attorney, Agent, or Firm* — Sughrue Mion, PLLC (57) ABSTRACT

Apparatus is configured to drive first action potentials orthodromically in a first direction along a nerve of a subject, and second action potentials orthodromically along the nerve in an opposite direction to the first direction. The apparatus includes: (1) first and second excitation units configured to be placed in a proximity of the nerve of the subject; (2) a blocking unit disposed between the excitation units and placeable in a proximity of the nerve of the subject; and (3) a control unit, configured: (i) to drive the first and second excitation units to apply, respectively, first and second excitatory currents to the nerve of the subject, and (ii) to drive the blocking unit to apply a blocking current to the nerve of the subject that blocks action potentials that propagate from the first and second excitatory units toward the blocking unit. Other embodiments are also described.

19 Claims, 5 Drawing Sheets

(56) References Cited

U.S. PATENT DOCUMENTS

| | | |
|---|---|---|
| 4,338,945 A | 7/1982 | Kosugi et al. |
| 4,392,496 A | 7/1983 | Stanton |
| 4,535,785 A | 8/1985 | Van Den Honert et al. |
| 4,542,753 A | 9/1985 | Brenman et al. |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples et al. |
| 4,608,985 A | 9/1986 | Crish et al. |
| 4,628,942 A | 12/1986 | Sweeney et al. |
| 4,632,116 A | 12/1986 | Rosen et al. |
| 4,649,936 A | 3/1987 | Ungar et al. |
| 4,663,102 A | 5/1987 | Brenman et al. |
| 4,702,254 A | 10/1987 | Zabara |
| 4,739,764 A | 4/1988 | Lue et al. |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,042,497 A | 8/1991 | Shapland |
| 5,058,599 A | 10/1991 | Andersen |
| 5,069,680 A | 12/1991 | Grandjean |
| 5,170,802 A | 12/1992 | Mehra |
| 5,178,161 A | 1/1993 | Kovacs |
| 5,188,104 A | 2/1993 | Wernicke et al. |
| 5,193,539 A | 3/1993 | Schulman et al. |
| 5,193,540 A | 3/1993 | Schulman et al. |
| 5,199,428 A | 4/1993 | Obel et al. |
| 5,199,430 A | 4/1993 | Fang et al. |
| 5,203,326 A | 4/1993 | Collins |
| 5,205,285 A | 4/1993 | Baker, Jr. |
| 5,215,086 A | 6/1993 | Terry, Jr. et al. |
| 5,224,491 A | 7/1993 | Mehra |
| 5,263,480 A | 11/1993 | Wernicke et al. |
| 5,282,468 A | 2/1994 | Klepinski |
| 5,292,344 A | 3/1994 | Douglas |
| 5,299,569 A | 4/1994 | Wernicke et al. |
| 5,312,439 A | 5/1994 | Loeb |
| 5,314,495 A | 5/1994 | Kovacs |
| 5,330,507 A | 7/1994 | Schwartz |
| 5,335,657 A | 8/1994 | Terry, Jr. et al. |
| 5,411,531 A | 5/1995 | Hill et al. |
| 5,423,872 A | 6/1995 | Cigaina |
| 5,437,285 A | 8/1995 | Verrier et al. |
| 5,439,938 A | 8/1995 | Snyder et al. |
| 5,454,840 A | 10/1995 | Krakovsky et al. |
| 5,505,201 A | 4/1996 | Grill, Jr. et al. |
| 5,507,784 A | 4/1996 | Hill et al. |
| 5,540,730 A | 7/1996 | Terry, Jr. et al. |
| 5,540,734 A | 7/1996 | Zabara |
| 5,562,718 A | 10/1996 | Palermo |
| 5,571,118 A | 11/1996 | Boutos |
| 5,571,150 A | 11/1996 | Wernicke et al. |
| 5,578,061 A | 11/1996 | Stroetmann et al. |
| 5,615,684 A | 4/1997 | Hagel et al. |
| 5,634,462 A | 6/1997 | Tyler et al. |
| 5,645,570 A | 7/1997 | Corbucci |
| 5,690,681 A | 11/1997 | Geddes et al. |
| 5,690,691 A | 11/1997 | Chen et al. |
| 5,700,282 A | 12/1997 | Zabara |
| 5,707,400 A | 1/1998 | Terry, Jr. et al. |
| 5,711,316 A | 1/1998 | Elsberry et al. |
| 5,716,385 A | 2/1998 | Mittal et al. |
| 5,748,845 A | 5/1998 | Labun et al. |
| 5,755,750 A | 5/1998 | Petruska et al. |
| 5,775,331 A | 7/1998 | Raymond et al. |
| 5,776,171 A | 7/1998 | Peckham et al. |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,938,584 A | 8/1999 | Ardito et al. |
| 5,954,758 A | 9/1999 | Peckham et al. |
| 6,026,326 A | 2/2000 | Bardy |
| 6,026,328 A | 2/2000 | Peckham et al. |
| 6,051,017 A | 4/2000 | Loeb et al. |
| 6,058,328 A | 5/2000 | Levine et al. |
| 6,058,331 A | 5/2000 | King |
| 6,061,596 A | 5/2000 | Richmond et al. |
| 6,066,163 A | 5/2000 | John |
| 6,073,048 A | 6/2000 | Kieval et al. |
| 6,083,249 A | 7/2000 | Familoni |
| 6,086,525 A | 7/2000 | Davey et al. |
| 6,091,922 A | 7/2000 | Bisaiji |
| 6,091,977 A | 7/2000 | Tarjan et al. |
| 6,091,992 A | 7/2000 | Bourgeois et al. |
| 6,094,598 A | 7/2000 | Elsberry et al. |
| 6,097,984 A | 8/2000 | Douglas |
| 6,104,955 A | 8/2000 | Bourgeois |
| 6,104,956 A | 8/2000 | Naritoku et al. |
| 6,104,960 A | 8/2000 | Duysens et al. |
| 6,119,516 A | 9/2000 | Hock |
| 6,146,335 A | 11/2000 | Gozani |
| 6,161,029 A | 12/2000 | Spreigl et al. |
| 6,167,304 A | 12/2000 | Loos |
| 6,169,924 B1 | 1/2001 | Meloy et al. |
| 6,205,359 B1 | 3/2001 | Boveja |
| 6,230,061 B1 | 5/2001 | Hartung |
| 6,240,314 B1 | 5/2001 | Plicchi et al. |
| 6,266,564 B1 | 7/2001 | Hill et al. |
| 6,272,377 B1 | 8/2001 | Sweeney et al. |
| 6,319,241 B1 | 11/2001 | King et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,366,813 B1 | 4/2002 | DiLorenzo |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,449,507 B1 | 9/2002 | Hill et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,522,926 B1 | 2/2003 | Kieval et al. |
| 6,542,774 B2 | 4/2003 | Hill et al. |
| 6,564,096 B2 | 5/2003 | Mest |
| 6,571,122 B2 | 5/2003 | Schroeppel et al. |
| 6,587,727 B2 | 7/2003 | Osorio et al. |
| 6,600,954 B2 | 7/2003 | Cohen et al. |
| 6,600,956 B2 | 7/2003 | Maschino et al. |
| 6,610,713 B2 | 8/2003 | Tracey |
| 6,622,041 B2 | 9/2003 | Terry, Jr. et al. |
| 6,628,987 B1 | 9/2003 | Hill et al. |
| 6,650,943 B1 | 11/2003 | Whitehurst et al. |
| 6,658,297 B2 | 12/2003 | Loeb |
| 6,668,191 B1 | 12/2003 | Boveja |
| 6,671,556 B2 | 12/2003 | Osorio et al. |
| 6,684,105 B2 | 1/2004 | Cohen et al. |
| 6,690,971 B2 | 2/2004 | Schauerte et al. |
| 6,733,485 B1 | 5/2004 | Whitehurst et al. |
| 6,735,474 B1 | 5/2004 | Loeb et al. |
| RE38,705 E | 2/2005 | Hill et al. |
| 6,862,479 B1 | 3/2005 | Whitehurst et al. |
| 6,865,416 B2 | 3/2005 | Dev et al. |
| 6,885,888 B2 | 4/2005 | Rezai |
| 6,892,098 B2 | 5/2005 | Ayal et al. |
| 6,895,280 B2 | 5/2005 | Meadows et al. |
| 6,907,293 B2 | 6/2005 | Grill et al. |
| 6,907,295 B2 | 6/2005 | Gross et al. |
| 6,928,320 B2 | 8/2005 | King |
| 6,934,583 B2 | 8/2005 | Weinberg et al. |
| 6,985,774 B2 | 1/2006 | Kieval et al. |
| 7,050,846 B2 | 5/2006 | Sweeney et al. |
| 7,076,299 B2 | 7/2006 | Thong |
| 7,076,307 B2 | 7/2006 | Boveja et al. |
| 7,123,961 B1 | 10/2006 | Kroll et al. |
| 7,263,405 B2 | 8/2007 | Boveja et al. |
| 7,324,853 B2 | 1/2008 | Ayal et al. |
| 7,489,969 B2 | 2/2009 | Knudson et al. |
| 7,734,355 B2 | 6/2010 | Cohen et al. |
| 7,778,703 B2 | 8/2010 | Gross et al. |
| 7,885,709 B2 | 2/2011 | Ben-David |
| 7,890,185 B2 | 2/2011 | Cohen et al. |

(56) References Cited

U.S. PATENT DOCUMENTS

| | | |
|---|---|---|
| 8,046,085 B2 | 10/2011 | Knudson et al. |
| 2001/0003799 A1 | 6/2001 | Boveja et al. |
| 2002/0035335 A1 | 3/2002 | Schauerte |
| 2002/0055761 A1 | 5/2002 | Mann et al. |
| 2002/0099419 A1 | 7/2002 | Cohen et al. |
| 2002/0107553 A1 | 8/2002 | Hill et al. |
| 2003/0018365 A1 | 1/2003 | Loeb |
| 2003/0040774 A1 | 2/2003 | Terry, Jr. et al. |
| 2003/0195574 A1 | 10/2003 | Osorio et al. |
| 2003/0216775 A1 | 11/2003 | Hill et al. |
| 2003/0229380 A1 | 12/2003 | Adams et al. |
| 2003/0233129 A1 | 12/2003 | Matos |
| 2003/0236557 A1 | 12/2003 | Whitehurst et al. |
| 2003/0236558 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0048795 A1 | 3/2004 | Ivanova et al. |
| 2004/0059392 A1 | 3/2004 | Parramon et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0215289 A1 | 10/2004 | Fukui |
| 2004/0249416 A1 | 12/2004 | Yun et al. |
| 2005/0131467 A1 | 6/2005 | Boveja |
| 2005/0187584 A1 | 8/2005 | Denker et al. |
| 2005/0222644 A1 | 10/2005 | Killian et al. |
| 2006/0015153 A1 | 1/2006 | Gliner et al. |
| 2006/0047325 A1 | 3/2006 | Thimineur et al. |
| 2006/0052831 A1 | 3/2006 | Fukui |
| 2006/0064140 A1 | 3/2006 | Whitehurst et al. |
| 2006/0074450 A1 | 4/2006 | Boveja et al. |
| 2006/0129205 A1 | 6/2006 | Boveja et al. |
| 2006/0149337 A1 | 7/2006 | John |
| 2006/0167498 A1 | 7/2006 | DiLorenzo |
| 2008/0119898 A1 | 5/2008 | Ben-David et al. |
| 2008/0132964 A1* | 6/2008 | Cohen et al. ........... A61B 5/412 607/5 |
| 2009/0149912 A1* | 6/2009 | Dacey, Jr. et al. .... A61N 1/0556 607/45 |
| 2011/0301670 A1 | 12/2011 | Gross et al. |
| 2012/0101326 A1* | 4/2012 | Simon et al. ....... A61N 1/36007 600/9 |
| 2012/0296389 A1* | 11/2012 | Fang et al. ........... A61N 1/0556 607/41 |
| 2013/0066393 A1 | 3/2013 | Gross et al. |

FOREIGN PATENT DOCUMENTS

| | | |
|---|---|---|
| WO | WO/98/37926 A1 | 9/1998 |
| WO | WO/98/43700 A1 | 10/1998 |
| WO | WO/98/43701 A1 | 10/1998 |
| WO | WO/01/10375 A2 | 2/2001 |
| WO | WO/01/10432 A1 | 2/2001 |
| WO | WO/01/26729 A1 | 4/2001 |
| WO | WO/02/058782 A2 | 8/2002 |
| WO | WO/2006/102370 A2 | 9/2006 |

OTHER PUBLICATIONS

European Office Action, issued Apr. 3, 2009, in connection with European Patent Application No. 02716294.0, filed Jan. 23, 2002.
Fang et al., 1991. "Selective activation of small motor axons by quasitrapezoidal current pulses". IEEE Transactions on Biomedical Engineering 38: 168-174.
Stampfli, Robert, 1954. "Saltatory conduction in nerve". Physiol. Rev. 34: 101-112.
Schaldach, M, "New concepts in electrotherapy of the heart", Electrotherapy of the Heart, Springer Verlag Heidelberg, pp. 210-214 (1992).
Advisory Action issued Mar. 4, 2003 during the prosecution of U.S. Appl. No. 09/824,682.
Office Action issued Jul. 17, 2002 during the prosecution of U.S. Appl. No. 09/824,682.
Final Office Action issued Jan. 23, 2003 during the prosecution of U.S. Appl. No. 09/824,682.
Rattay, F., (1989) "Analysis of models for extracellular fiber stimulation," IEEE Transactions on Biomedical Engineering, 36(2): 676-682.
Office Action issued Nov. 1, 2007, in connection with U.S. Appl. No. 10/205,475.
Jones, J.F.X. et al., (1998) "Activity of C Fibre Cardiac Vagal Efferents in Anaesthetized Cats and Rats," Journal of Physiology, 507(3) 869-880.
Office Action, issued Apr. 5, 2007, in connection with U.S. Appl. No. 10/488,334.
Office Action, issued Apr. 25, 2008, in connection with U.S. Appl. No. 10/488,334.
Rijkhof, N. J. M. et al. "Acute Animal Studies on the Use of Anodal Block to Reduce Urethral Resistance in Sacral Root Stimulation,", IEEE Transactions on Rehabilitation Engineering, vol. 2, No. 2, pp. 92, 1994.
Office Action, issued Feb. 13, 2004, in connection with U.S. Appl. No. 10/254,024, filed Sep. 24, 2002.
Office Action, issued Dec. 26, 2008, in connection with U.S. Appl. No. 10/488,334.
Website: http://www.bcm.tmc.edu/neurol/struct/epilep/epilipsy.sub.--vagus.- html, May 31, 2001.
Office Action, issued Apr. 7, 2006, in connection with U.S. Appl. No. 10/722,589.
Office Action, issued Jan. 5, 2007, in connection with U.S. Appl. No. 10/722,589.
Office Action, issued May 14, 2008, in connection with U.S. Appl. No. 10/722,589.
Office Action, issued Mar. 17, 2010, in connection with U.S. Appl. No. 10/722,589.
Davis R. "Cerebellar stimulation for cerebral palsy spasticity, function, and seizures," Archives of Medical Research 31:290-299 (2000).
Mushahwar V K et al. "Muscle recruitment through electrical stimulation of the lumbo-sacral spinal cord," IEEE Trans Rehabil Eng, 8(1):22-9 (2000).
Deurloo K E et al., "Transverse tripolar stimulation of peripheral nerve: a modelling study of spatial selectivity," Med Biol Eng Comput, 36(1):66-74 (1998).
Tarver W B et al. "Clinical experience with a helical bipolar stimulating lead," Pace, vol. 15, October, Part II (1992).
Agnew W F et al. "Microstimulation of the lumbosacral spinal cord," Huntington Medical Research Institutes Neurological Research Laboratory, Sep. 30, 1995-Sep. 29, 1998.
Grill W M et al. "Inversion of the current-distance relationship by transient depolarization," IEEE Trans Biomed Eng, 44 (1):1-9 (1997).
Goodall E V et al., "Position-selective activation of peripheral nerve fibers with a cuff electrode," IEEE Trans Biomed Eng, 43(8):851-6 (1996).
Veraart C et al., "Selective control of muscle activation with a multipolar nerve cuff electrode," IEEE Trans Biomed Eng, 40(7):640-53 (1993).
Zhang, Deyuan et al. "Fabrication of graded TiN coatings on nitinol occluders and effects on in vivo nickel release" Bio-Medical Materials and Engineering, 18(6): 387-393 (2008).
Van Den Honert, C and Mortimer, J.T. "Generation of unidirectionally propagated action potentials in a peripheral nerve by brief stimuli" Science, 206 (4424): 1311-1312 (1979).
Zabara, Jacob "Inhibition of Experimental Seizures in Canines by Repetitive Vagal Stimulation" Epilepsia, 33(6): 1005-1012 (1992).
Zhang, Xu et al. "Mechanism of Nerve Conduction Block Induced by High-Frequency Biphasic Electrical Currents" Biomedical Engineering, IEEE Transactions, 53(12): 2445-2454 (2006).
Mortimer J. Thomas and Bhadra, Narendra "Peripheral Nerve and Muscle Stumulation" Chapter 4.2 in 'Neuroprosthetics, Theory and Practice' book, published by World Scientific, pp. 1-48 (2004).
Tuday, Eric C. et al. "Differential activation of nerve fibers with magnetic stimulation in humans" BMC Neuroscience, 7: 58. Published online Jul. 24, 2006. doi: 10.1186/1471-2202-7-58.

(56) References Cited

OTHER PUBLICATIONS

U.S. Appl. No. 60/263,834 "Selected Blocking of Nerve Fibers" to Cohen and Ayal, filed Jan. 25, 2001.
Ungar, Ira J. et al. "Generation of undirectionally propagating action potentials using a monopolar electrode cuff", Annals of Biomedical Engineering, vol. 14, pp. 437-450, 1986.
Sweeney, James D. et al. "An asymmetric two electrode cuff for generation of undirectionally propagated action potentials", IEEE Transactions on Biomedical Engineering, vol. BME-33, No. 6, Jun. 1986.
Naples, Gregory G. et al. "A spiral nerve cuff electrode for peripheral nerve stimulation" IEEE Transactions on Biomedical Engineering, vol. 35, No. 11, Nov. 1988.
Sweeney, James D. et al. "A nerve cuff technique for selective excitation of peripheral nerve trunk regions" IEEE Transactions on Biomedical Engineering, vol. 37, No. 7, Jul. 1990.
Office Action dated Jun. 27, 2008 which was issued during the prosecution of Applicant's U.S. Appl. No. 10/205,475.
Van Den Honert, C and Mortimer, J.T. "A technique for collision block of peripheral nerve: Frequency dependence" MP-12, IEEE Transactions on Biomedical Engineering, 28:379-382, 1981.
Fitzpatrick, M. et al., "A nerve cuff design for the selective activation and blocking of myelinated nerve fibers", D Ann. Conf. of the IEEE Engineering in Medicine and Biology Soc., vol. 13, No. 2, pp. 906, 1991.
Rijkhoff, N.J.M. et al. "Orderly recruitment of motoneurons in an acute rabit model"Ann. Conf. of the IEEE Eng., Medicine and Biology Soc., vol. 20, No. 5, pp. 2564-2565, 1998.
Baratta, R. et al. "Orderly stimulation of skeletal muscle motor units with tripolar nerve cuff electrode", , IEEE Transactions on Biomedical Engineering, vol. 36, No. 8, pp. 836-843, 1989.
Devor, M. "Pain Networks", Handbook of Brain Theory and Neural Networks, Ed. M.A. Arbib, MIT Press, pp. 698, 1998.
Manfredi, M. "Differential Block of Conduction of larger fibers in peripheral nerve by direct current", Arch. Ital. Biol. 108:52-71, 1970.
Cortese, J.F. "Vagus Nerve Stimulation for Control of Intractable Epileptic Seizures", available at: http://www.science.wayne.edu/.about.bio340/StudentPages/cortese/, May 31, 2001.
Sweeney, James D. et al. "An asymmetric two electrode cuf for generation of undirectionally propagated action potentials", IEEE Transactions on Biomedical Engineering, vol. BME-33, No. 6, Jun. 1986.
Evetovich, T.K. et al., "Gender comparasions of the mechanomyographic responses to maximal concentric and eccentric isokinetic muscle actions", Medicine & Science in Sports & Exercise, 1998, 30(12), pp. 1697-1702.
Cohen and Ayal, "Selective control of nerve fibers", Filed Jan. 2, 2001, U.S. Appl. 60/263,834.
Zhang, Youhua , et al., "Optimal vertricular rate slowing during atrial fibrillation by feedback AV nodal-selective vagal stimulation", Am J. Phyocal Heart Circ Physiol 282:H1102-H1110, 2002.
Jones et al. "Heart rate responses to selective stimulationof cardiac vagal fibres in anaesthetized cats, rats and rabbits" Journal of Physiology 1995;489; 203-214.
Wallick, Don W. et al "Selective AV nodal vagal stimulation improves hemodynamics during acute atrial fibrillation in dogs", Am J. Physiol Heart Circ Physiol, 281: H1490-H1497, 2001.
Tsuboi, Masato et al., "Inotropic, chronotropic and dromotropic effects mediated via parasympathetic ganglia in the dog heart", Am J. Physiol Heart Circ Physiol, 279: H1201-H1207, 2000.
Chiou, C.W. et al., "Efferent vagal innervation of the canine atria and sinus and atrioventricular nodes", Circulation, 1997; 95:2573.
Schauerte, P. et al, "Catheter stimulation of cariac parasympathetic nerves in humans", available at http://www.circulationaha.org, pp. 2430-2435, 2001.
Hirose, M. "Pituitary adenylate cyclase-activating polypeptide-27 causes a biphasic chronotropic effect and atrial fibrillation in autonomically decentralized, anesthetized dogs", The Journal of Pharmacology and Experimental Therapeutics, vol. 283, No. 2, pp. 478-487, 1997.
Furukawa, Y. et al., "Differential blocking effects of atropine and gallamine on negative chrontropic and dromotropic responses to vagus stimulation in anesthetized dogs," J Pharmacol Exp. Ther. 251(3):797-802 (1989).
Bluemel, K.M, "Parasympathetic postganglionic pathways to the sinoatrial node," J Physiol. 259 (5 Pt 2): H1504-10 (1990).
Garrigue, S. et al., "Post-ganglionic vagal stimulation of the atrioventricular node reduces ventricular rate during atrial fibrillation," Pace 21(4), Part II, 878 (1998).
Bibevski, S. et al. "Ganglionic Mechanisms Contribute to Diminished Vagal Control in Heart Failure," Circulation 99:2958-2963(1999).
Chen, S.A. et al., "Intracardiac stimulation of human parasympathetic nerve fibers induces negative dromotropic effects: implication with the lesions of radiofrequency catheter ablation," J Cardiovasc Electrophysiol. 9(3):245-52 (1998).
Cooper et al., "Neural effects on sinus rate and atrial ventricular conduction produced by electrical stimulation from a transvenous electrode catheter in the canine right pulmonary artery" Circ Res vol. 46(1):48-57 (1980).
Waninger, M.S. et al., "Electrophysiological control of ventricular rate during atrial fibrillation," Pace 23:1239-1244 (2000).
Goldberger, J.J. et al., "New technique for vagal nerve stimulation," J Neurosci Methods. 91(1-2):1089-14 (1999).
Carlson, M.D. et al., "Selective stimulation of parasympathetic nerve fibers to the human sinoatrial node," Circulation 85:1311-1317 (1992).
Page, P.L. et al., "Regional distribution of atrial electrical changes induced by stimulation of extracardiac and intracardia neural elements," J. Thorac Cardiovasc Surg. 109(2):377-388 (1995).
Zi-Ping, Fang, et al., (1991) "Selective Activation of Small Motor Axons by Quasitrapezodial Current Pulses", IEEE Transactions on Biomedical Engineering 38(2): 168-171.

* cited by examiner

INDEPENDENTLY-CONTROLLED BIDIRECTIONAL NERVE STIMULATION

CROSS-REFERENCES TO RELATED APPLICATIONS

The present application claims priority from U.S. Provisional Patent Application 61/806,448 to Gross, filed Mar. 29, 2013, and entitled "Independently-controlled bidirectional nerve stimulation," which is incorporated herein by reference.

FIELD OF THE INVENTION

Some applications of the present invention generally relate to medical apparatus. Specifically, some applications of the present invention relate to apparatus and methods for initiating and blocking action potentials in nerves.

BACKGROUND

Nerve stimulation is used and/or proposed for use in treating certain medical conditions, including epilepsy, heart failure and tremor. Typically, an action potential that is artificially initiated at a site on an axon of the nerve (e.g., midway along a nerve), propagates in both directions (e.g., in orthodromic and antidromic directions) along the nerve. For some conditions, this precludes the use of nerve stimulation-based treatment, e.g., due to an undesired effect on an anatomical site (e.g., a non-target anatomical site) that is at the opposite end of the nerve to the anatomical site being treated (i.e., the target site).

In some cases, a blocking device is used to apply a blocking current behind the initiated action potential, so as to block the action potential from propagating to the non-target anatomical site.

SUMMARY OF THE INVENTION

For some applications of the invention, apparatus is provided, including at least two excitation units and at least one blocking unit, disposed between the excitation units. The apparatus typically comprises a nerve cuff, which is placed around a nerve of a subject. Each excitation unit is configured to initiate action potentials at a site of the nerve near the excitation unit. The blocking unit is configured to block action potentials at a site of the nerve near the blocking unit (and between the sites of the nerve near the two excitation units). The apparatus is thereby configured to initiate independently-controllable action potentials in two directions along the nerve. Typically, the apparatus is coupled to a nerve of a subject in whom two or more anatomical sites are to be treated.

There is therefore provided, in accordance with an application of the present invention, apparatus for stimulating a nerve of a subject, the apparatus being configured to drive first action potentials orthodromically in a first direction along the nerve, and second action potentials orthodromically along the nerve in an opposite direction to the first direction, the apparatus including:

a first excitation unit and a second excitation unit, the excitation units being configured to be placed in a proximity of the nerve of the subject;

a blocking unit disposed between the excitation units and configured to be placeable in a proximity of the nerve of the subject; and a control unit, configured:
to drive the first excitation unit to apply a first excitatory current to the nerve of the subject,
to drive the second excitation unit to apply a second excitatory current to the nerve of the subject, and
to drive the blocking unit to apply a blocking current to the nerve of the subject that blocks action potentials that propagate from the first and second excitatory units toward the blocking unit.

In an application, the control unit is configured to configure the blocking current to have a frequency of greater than 50 Hz.

In an application, the blocking unit includes at least one blocking electrode.

In an application, the control unit is configured to apply the blocking current as a high frequency (HF) blocking current.

In an application, the apparatus is configured:
to apply the first excitatory current to a first portion of the nerve,
to apply the second excitatory current to a second portion of the nerve, and
to apply the blocking current to a third portion of the nerve that is disposed between the first and second portions of the nerve.

In an application:
the apparatus includes at least a first electrode, a second electrode, a third electrode, and a fourth electrode, and
the control unit is configured:
to define the first excitation unit from at least the first electrode and the second electrode,
to define the second excitation unit from at least the third electrode and the fourth electrode, and
to define the blocking unit from at least the second electrode and the third electrode.

In an application, the control unit is configured to drive the first excitation unit to apply the first excitatory current independently from driving the second excitation unit to apply the second excitatory current.

In an application, the control unit is configured to at least sometimes drive the first excitation unit to apply the first excitatory current at least 5 minutes away from a closest application of the second excitatory current by the second excitation unit.

In an application, the control unit is configured to at least sometimes drive the first excitation unit to apply the first excitatory current at least 6 months away from a first application of the second excitatory current by the second excitation unit.

In an application, the control unit is configurable to not drive the first excitation unit to apply the first excitatory current, and to subsequently be reconfigured to drive the first excitation unit to apply the first excitatory current.

In an application, the apparatus further includes a nerve cuff, and the excitation units and the blocking unit are disposed on the nerve cuff.

In an application:
each excitation unit includes at least one excitation electrode,
the blocking unit includes at least one blocking electrode,
the nerve cuff is shaped to define a lumen, and has an inner surface, and
the excitation electrodes and the blocking electrodes are disposed on the inner surface of the nerve cuff.

In an application, the nerve cuff has two ends, and each excitation unit is disposed closer to a respective one of the ends than is the blocking unit.

In an application, each excitation unit includes at least one electrode.

In an application, each excitation unit includes two or more electrodes.

In an application, the control unit is configured to:

configure the first excitatory current to initiate propagation of first action potentials in the nerve of the subject, configure the second excitatory current to initiate propagation of second action potentials in the nerve of the subject, direct the first action potentials in a first direction along the nerve of the subject, and direct the second action potentials in a second direction along the nerve of the subject.

In an application, the control unit is configured to direct the first action potentials in the first direction and the second action potentials in the second direction, by inhibiting propagation of the first action potentials in the second direction and propagation of the second action potentials in the first direction, by driving the blocking unit to apply the blocking current to the nerve of the subject.

In an application, the control unit is configured to direct the first action potentials toward a site in a central nervous system of the subject.

In an application, the control unit is configured to direct the first action potentials toward a brain of the subject.

In an application, the control unit is configured to direct the second action potentials toward a heart of the subject.

In an application, the control unit is configured to direct the second action potential toward a muscle of the subject.

In an application, the control unit is configured to direct the second action potential toward a gastrointestinal organ of the subject.

In an application, the control unit is configured to initiate the propagation of the first and second action potentials in the vagus nerve of the subject.

In an application, the apparatus further includes a sensor, configured to detect a factor indicative of a state of the subject, and the control unit is configured to drive at least the first blocking unit to apply at least the first excitatory current in response to the detected factor.

In an application, the sensor is coupled to the control unit.

In an application, the sensor includes an implantable sensor.

In an application, the sensor includes an extracorporeal sensor.

There is further provided, in accordance with an application of the present invention, a method for treating a subject, the method including:

initiating propagation of a first action potential in a first direction along a nerve of the subject, by driving a first excitatory current via a first electrode;

initiating propagation of a second action potential in a second direction along the nerve of the subject, by driving a second excitatory current via a second electrode;

inhibiting propagation of the first action potential in the second direction; and inhibiting propagation of the second action potential in the first direction.

In an application, initiating propagation of the first and second action potentials includes initiating propagation of the first and second action potentials in a vagus nerve of the subject.

In an application, initiating propagation of the first action potential in the first direction along the nerve includes initiating propagation of the first action potential orthodromically in the first direction along the nerve, and initiating propagation of the second action potential in the second direction along the nerve includes initiating propagation of the second action potential orthodromically in the second direction along the nerve.

In an application, initiating propagation of the first action potential includes treating a first condition of the subject.

In an application, initiating propagation of the second action potential includes treating a second condition of the subject.

In an application, the method further includes detecting a factor indicative of a condition of a subject, and initiating propagation of the first action potential includes initiating propagation of at least the first action potential in response to detecting the factor.

In an application, detecting the factor includes detecting a movement of part of the subject, and initiating propagation of the first action potential includes initiating propagation of the first action potential in response to the detected movement.

In an application, detecting the factor includes detecting a tremor of part of the subject, and initiating propagation of the first action potential includes initiating propagation of the first action potential in response to the detected tremor.

In an application, initiating propagation of the first action potential includes initiating propagation of the first action potential toward a site in a central nervous system of the subject.

In an application, initiating propagation of the first action potential includes initiating propagation of the first action potential toward a brain of the subject.

In an application, initiating propagation of the second action potential includes initiating propagation of the second action potential toward a heart of the subject.

In an application, initiating propagation of the second action potential includes initiating propagation of the second action potential toward a site in a muscle of the subject.

In an application, initiating propagation of the second action potential includes initiating propagation of the second action potential toward a gastrointestinal organ of the subject.

In an application, at least inhibiting propagation of the first action potential includes driving a blocking current into the nerve of the subject.

In an application:

driving the first excitatory current includes driving the first excitatory current into a first portion of the nerve;

driving the second excitatory current includes driving the second excitatory current into a second portion of the nerve; and driving the blocking current includes driving the blocking current into a portion of the nerve that is disposed between the first and second portions of the nerve.

In an application, driving the blocking current includes driving an anodal blocking current.

In an application, driving the blocking current includes driving a high frequency blocking current.

There is further provided, in accordance with an application of the present invention, a method for treating a subject, including:

treating a first condition of the subject by directing first action potentials orthodromically in a first direction along a nerve of the subject, and treating a second condition of the subject by independently directing second action potentials orthodromically in a second direction along the nerve of the subject.

There is further provided, in accordance with an application of the present invention, a method for treating a subject, including:

identifying a subject as suffering from a first condition and a second condition; and treating the first and second conditions by facilitating, by implanting apparatus in a vicinity of a nerve of the subject:

initiation of propagation of a first action potential in a first direction along a nerve of the subject, initiation of propagation of a second action potential in a second direction along the nerve of the subject, and inhibition of propagation of the first action potential in the second direction and;

inhibition of propagation of the second action potential in the first direction.

In an application, implanting the apparatus in a vicinity of a nerve of the subject, includes implanting the apparatus in a vicinity of a vagus nerve of the subject.

In an application, identifying the subject as suffering from the first condition includes identifying the subject as suffering from epilepsy.

In an application, implanting apparatus includes implanting apparatus that includes:

a first excitation unit, configured to initiate the propagation of the first action potential by applying a first excitatory current to a first portion of the nerve of the subject, a second excitation unit, configured to initiate the propagation of the second action potential by applying a second excitatory current to a second portion of the nerve of the subject, and a blocking unit, configured to inhibit the propagation of the first action potential in the second direction, and propagation of the second action potential in the first direction, by applying a blocking current to a site that is disposed between the first and second portions of the nerve of the subject.

In an application, implanting the apparatus includes implanting the apparatus such that the first excitation unit initiates propagation of the first action potential toward a site in a central nervous system of the subject.

In an application, implanting the apparatus includes implanting the apparatus such that the first excitation unit initiates propagation of the first action potential toward a brain of the subject.

In an application, implanting the apparatus includes implanting the apparatus such that the second excitation unit initiates propagation of the second action potential toward a heart of the subject.

In an application, implanting the apparatus includes implanting the apparatus such that the second excitation unit initiates propagation of the second action potential toward a muscle of the subject.

In an application, implanting the apparatus includes implanting the apparatus such that the second excitation unit initiates propagation of the second action potential toward a gastrointestinal organ of the subject.

There is further provided, in accordance with an application of the present invention, apparatus for stimulating a nerve of a subject, the apparatus being configured:

to drive first action potentials orthodromically in a first direction along the nerve, to drive second action potentials orthodromically in a second direction along the nerve that is opposite to the first direction, to inhibit the first action potentials from moving in the second direction along the nerve, and to inhibit the second action potentials from moving in the first direction along the nerve.

There is further provided, in accordance with an application of the present invention, apparatus for use with a nerve of a subject, the apparatus including a nerve cuff, configured:

to initiate first action potentials in the nerve, and to direct the first action potentials in a first direction along the nerve and not in a second direction along the nerve, and to independently initiate second action potentials in the nerve, and to direct the second action potentials in the second direction along the nerve and not in the first direction along the nerve.

There is further provided, in accordance with an application of the present invention, apparatus for use with a nerve of a subject, the apparatus including:

a first excitation unit, configured to initiate action potentials in the nerve; and a second excitation unit, configured to initiate action potentials in the nerve, and the apparatus is arranged to provide a blocking unit, disposed between the first excitation unit and the second excitation unit, and configured to block propagation of action potentials along the nerve.

The present invention will be more fully understood from the following detailed description of applications thereof, taken together with the drawings, in which:

DETAILED DESCRIPTION OF EMBODIMENTS

Figure 1A:
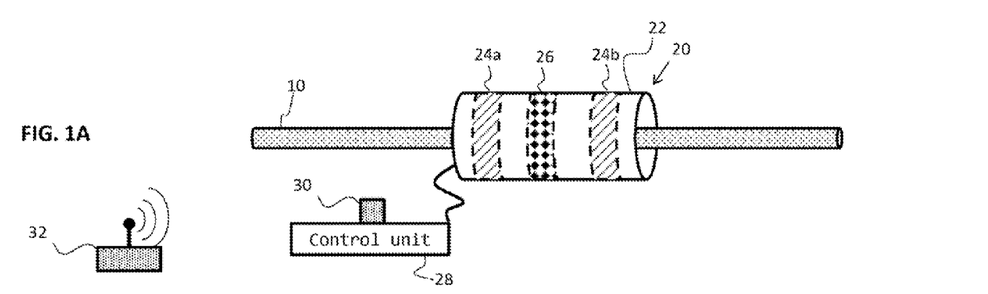
FIGS. 1A-B are schematic illustrations of apparatus for stimulating a nerve of a subject, in accordance with some applications of the invention.
Figure 1B:
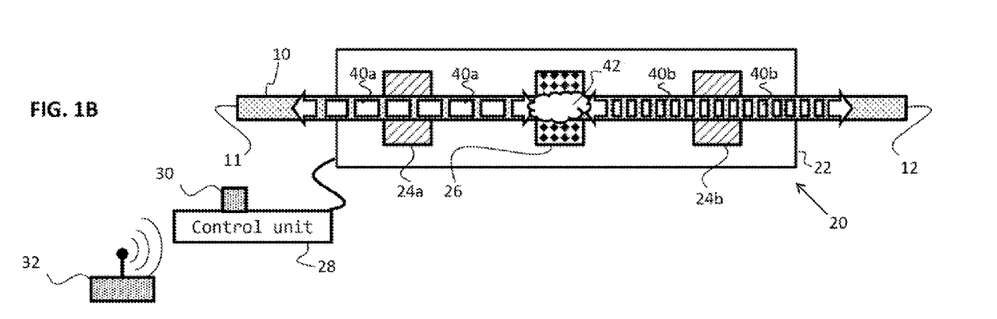

Reference is made to FIGS. 1A-B, which are schematic illustrations of apparatus 20, for independently-controlled bi-directional stimulation of a nerve 10 of a subject, in accordance with some applications of the invention. FIG. 1A is a perspective illustration of apparatus 20. Apparatus 20 comprises at least two excitation units 24, and at least one blocking unit 26. Typically, apparatus 20 comprises two excitation units: 24a and 24b, and one blocking unit 26. Blocking unit 26 is disposed between excitation units 24a and 24b. Typically, the excitation and blocking units are controlled by a control unit 28.

Excitation units 24a and 24b typically each comprise one or more electrodes, and are configured to stimulate nerve 10, i.e., to initiate propagation of action potentials in the nerve. Typically, initiation of propagation of the action potential is achieved by passing an excitatory current between at least a first electrode of an excitation unit and another electrode, so as to depolarize a site on the nerve. For example, a current may be driven between two electrodes of an excitation unit.

Typically apparatus 20 comprises a nerve cuff 22, configured to be placeable on (e.g., around) the nerve. Typically, following placement, nerve cuff 22 defines (1) a lumen, in which at least part of the nerve is disposed, (2) an inner surface, on which the electrodes of the excitation and blocking units are disposed, and (3) two open ends. Excitation units 24a and 24b are disposed on cuff 22, closer to the open ends than is blocking unit 26. That is, each excitation unit is disposed closer to a respective open end than is the blocking unit. Thereby, when nerve cuff 22 is placed on the nerve, each excitation unit is disposed closer to a respective end of the nerve than is the other excitation unit.

An action potential that is initiated (typically artificially) midway along a nerve axon, typically propagates in both directions along the axon, i.e., both orthodromically (e.g., toward axon terminals) and antidromically (e.g., toward the perikaryon of the neuron). Furthermore, electrical excitation of a nerve that comprises a plurality of nerve axons, such as a mixed nerve that comprises both afferent (e.g., sensory) and efferent (e.g., motor) axons, may initiate action potentials that propagate orthodromically and antidromically in many (e.g., all) of the axons. Typically, artificially-initiated action potentials are configured to have an effect on an anatomical site at one end of a nerve, and it is typically undesirable for these action potentials to reach a site at the other end of the nerve. For example, an electrical stimulation may be used to initiate a first action potential that is intended to propagate orthodromically along an afferent neuron, so as to have an effect on the brain; it is typically undesirable (1) for this first action potential to propagate antidromically along the afferent axon to an organ (e.g., the stomach), and/or (2) for the electrical stimulation to simultaneously initiate a second action potential in an efferent axon, such that the second action potential propagates orthodromically along the efferent neuron to the organ.

Typically, nerve 10 has a plurality of axons, and typically is a mixed nerve. Nerve cuff 22 is typically disposed around nerve 10, and thereby around the plurality of axons. It is thereby typically desirable to control directionality of action potential propagation, and/or in which axons action potentials are initiated.

Blocking unit 26 is configured to inhibit (e.g., block) propagation of action potentials past the blocking unit, by applying a blocking current to nerve 10. Thereby, although action potentials initiated by each excitation unit originally propagate in both directions along nerve 10, apparatus 20 causes the action potentials to, in effect, propagate only in the direction that is away from blocking unit 26. Thereby, apparatus 20 is configurable to initiate, in different (e.g., opposite) directions, the propagation of different action potentials (e.g., different action potential patterns). That is, apparatus 20 is configurable to direct different action potentials in different directions along the nerve of the subject.

For some applications, apparatus 20 is configurable to initiate and/or block action potentials in specific types of nerve fibers. For example, excitation and/or blocking currents having low intensity (e.g., amplitude) may be selected, so as to target initiation and/or blocking of action potentials to A nerve fibers, which are generally more susceptible to electrical manipulation than are B or C nerve fibers. Alternatively or additionally, high intensity (e.g., amplitude) of excitatory and/or blocking currents may be selected, so as to cause initiation and/or blocking of action potentials in all nerve fibers.

FIG. 1B is a cross-sectional schematic illustration of apparatus 20, coupled to nerve 10. Excitation unit 24a is configured to initiate action potentials 40a in nerve 10. Excitation unit 24b is configured to initiate action potentials 40b in nerve 10. Typically, control unit 28 controls the initiation of the action potentials. For some applications, the action potentials are initiated according to a specified (e.g., pre-defined) pattern, and action potentials 40a and 40b differ in some characteristic thereof, e.g., frequency, duty cycle, time-of-day of generation, and/or reason for generation of the action potentials (such as a detected parameter in response to which only action potentials 40a are generated, but not action potentials 40b). For some applications, the action potentials are initiated at least in part responsively to detected parameters. For some such applications, apparatus 20 comprises a sensor 30, configured to detect one or more factors (e.g., factors indicative of a state of the subject), and to responsively generate a signal indicative of the detected factors, and control unit 28 drives the excitation units to initiate the action potentials in response to the signal. Typically, sensor 30 is implantable, and further typically, is integrated with control unit 28 and/or nerve cuff 22. Alternatively or additionally, apparatus 20 may comprise an external sensor 32, configured to extracorporeally detect one or more factors, and to generate a signal (e.g., a wireless signal) in response to the detected factors. For some applications, extracorporeal sensor 32 may alternatively or additionally wirelessly transmit power, and control unit 28 is configured to be powered by the wireless power.

Blocking unit 26 typically comprises at least one electrode, and applies a blocking current 42 into nerve 10. Typically, control unit 28 drives the application of the blocking current by blocking unit 26. As described hereinabove (e.g., with reference to FIG. 1A), blocking unit 26 blocks propagation of action potentials past the blocking unit. That is, blocking unit 26 blocks (1) propagation of action potential 40a past the blocking unit, toward end 12 of nerve 10, and (2) propagation of action potential 40b past the blocking unit, toward end 11 of nerve 10.

In this way, action potentials having different characteristics (e.g., patterns) can be propagated in different (e.g., opposite) directions along the same nerve. That is, apparatus 20 (e.g., control unit 28 thereof) is configurable to direct action potentials 40a in one direction and action potentials 40b in another direction along the same nerve. For example, action potential 40a may be initiated in response to a first detected parameter, and configured to have an effect on a first anatomical site, and action potential 40b may be initiated in response to a second detected parameter, and configured to have an effect on a second anatomical site. Alternatively or additionally, action potential 40a may be initiated at a first frequency, so as to have an effect on the first anatomical site, and action potential 40b may be initiated at a second frequency, so as to have an effect on a second anatomical site.

Typically, apparatus 20 is used to treat subjects suffering from two conditions, such that the effect on the first anatomical site treats a first condition, and the effect on the second anatomical site treats a second condition. Non-limiting examples of such pairs of conditions are described hereinbelow, with reference to FIGS. 4-5.

Typically, blocking unit 26 and/or control unit 28 configures blocking current 42 to be a high frequency (HF) current that has a frequency of greater than 50 Hz (e.g., greater than 1 kHz, such as greater than 5 kHz), to induce HF blocking of nerve 10. Alternatively or additionally, blocking unit 26 and/or control unit 28 configures blocking current 42 to be an anodal blocking current.

Figure 2A:
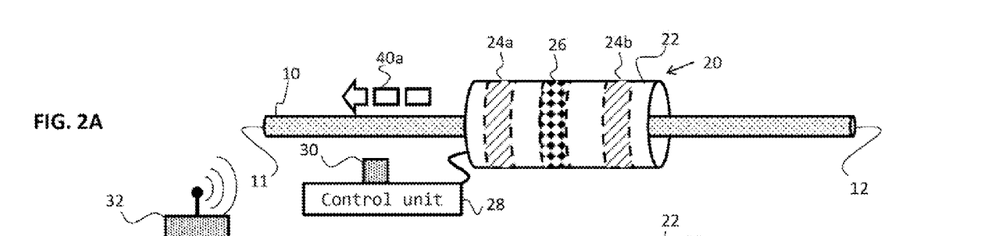
FIGS. 2A-C are schematic illustrations of various states of the apparatus, in accordance with some applications of the invention.
Figures 2B, 2C:
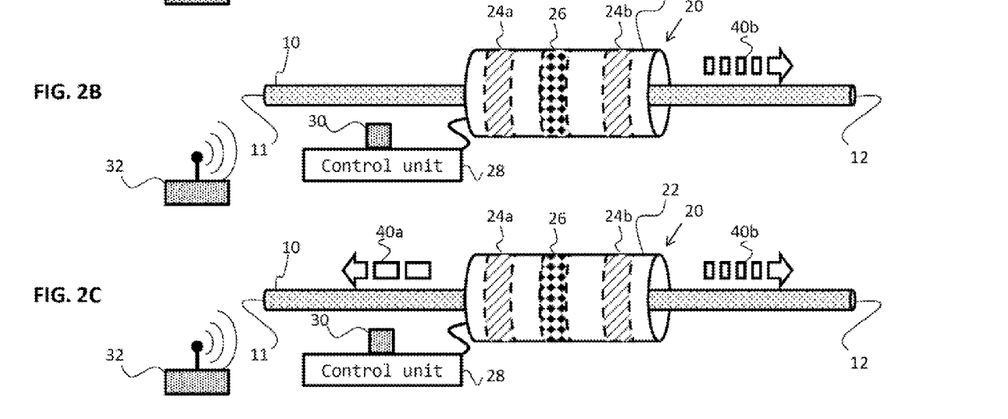

Reference is now made to FIGS. 2A-C, which are schematic illustrations of various states of apparatus 20 initiating action potentials, in accordance with some applications of the invention. FIG. 2A shows action potentials 40a having been initiated by excitation unit 24a, and blocked by blocking unit 26, and thereby propagating toward only end 11 of nerve 10 (i.e., not propagating toward end 12 of the nerve). FIG. 2B shows action potentials 40b having been initiated by excitation unit 24b, and blocked by blocking unit 26, and thereby propagating toward only end 12 of nerve 10 (i.e., not propagating toward end 11 of the nerve).

FIG. 2C shows action potentials 40a and 40b having been initiated during the same time period by excitation units 24a and 24b, respectively. Action potentials 40a and 40b propagating toward blocking unit 26 are blocked by blocking unit 26, and thereby action potentials 40a propagate only toward end 11 of nerve 10, and action potentials 40b propagate only toward end 12 of nerve 10. Apparatus 20 thereby advantageously facilitates the initiation of independent (e.g., different) action potentials in opposite directions along the same nerve. For some applications, control unit 28 is configured to initiate action potentials 40a and 40b at different times. For some such applications, control unit 28 is configured to at least sometimes drive action potentials 40a at least 5 minutes away from a closest application of action potentials 40b. For some applications, control unit 28 is configured to drive action potentials 40a (e.g., to first drive action potentials 40a) at least 6 months away from a first application of action potentials 40b. For some applications, control unit 28 is configurable (e.g., by a physician, such as via an extracorporeal adjusting device) to start and/or stop initiating one or more of the action potentials. For example, apparatus 20 may be implanted in a first state in which control unit 28 drives first excitation unit 24a to initiate action potentials 40a, but does not drive second excitation unit 24b to initiate action potentials 40b, and may be subsequently (e.g., soon after implantation and/or long after implantation) reconfigured to a second state in which the control unit drives second excitation unit 24b to initiate action potentials 40b, and/or no longer drives first excitation unit 24a to initiate action potentials 40a.

For some applications of the invention, control unit 28 drives blocking unit 26 to apply blocking current 42 only when (e.g., at the same time and/or soon after) at least one of the action potentials is initiated (e.g., when at least one of the excitation units applies an excitatory current).

Figure 3:
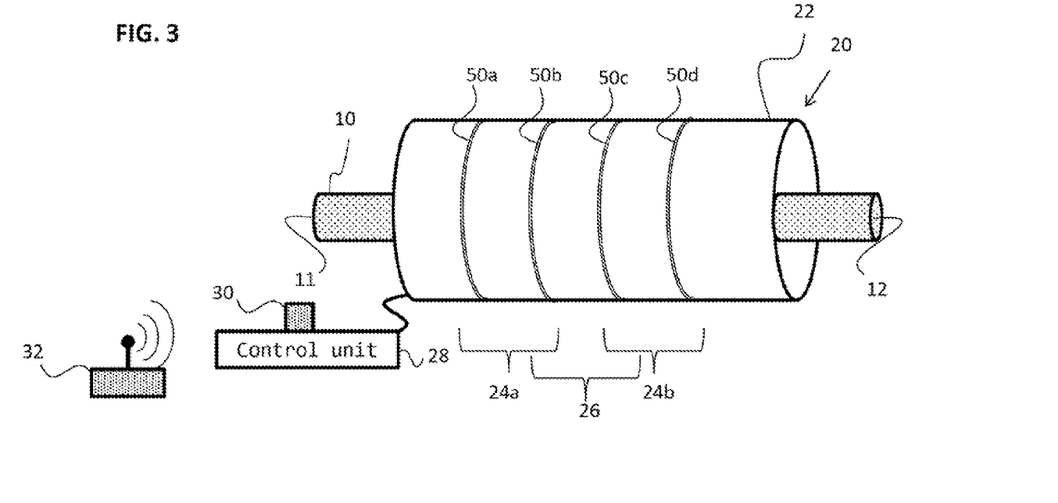
FIG. 3 is a schematic illustration of apparatus for stimulating a nerve of a subject, in accordance with some applications of the invention.

Reference is again made to FIGS. 1A-2C, and is made to FIG. 3, which is a schematic illustration of apparatus 20, in accordance with some applications of the invention. As described hereinabove, initiation of propagation of action potentials is typically achieved by passing an excitatory current between at least a first electrode of an excitation unit and another electrode. For some applications, each excitation unit comprises a plurality of (e.g., two) electrodes, and the action potentials are initiated by passing the excitatory current between the two electrodes of the excitation unit. For some applications, the action potentials are initiated by passing the excitatory current between an electrode of the excitation unit and an electrode of the blocking unit. For example, each excitation unit may comprise only one electrode.

For some such applications, and as shown in FIG. 3, apparatus 20 thereby typically comprises at least four electrodes 50, e.g., four electrodes 50 (e.g., a first electrode 50a, a second electrode 50b, a third electrode 50c, and a fourth electrode 50d), disposed along a longitudinal axis of apparatus (e.g., along a longitudinal axis of nerve cuff 22). Electrodes 50b and 50c are disposed between electrodes 50a and 50d. Blocking unit 26 comprises electrodes 50b and 50c. Excitation unit 24a comprises electrodes 50a and 50b, and excitation unit 24b comprises electrodes 50c and 50d. That is, apparatus 20 employs electrodes 50b and 50c for driving of both the blocking signal and the excitatory signals. That is, control unit 28 is configured (i) to define first excitation unit 24a from first electrode 50a and second electrode 50b, (ii) to define second excitation unit 24b from third electrode 50c and fourth electrode 50d, and (iii) to define blocking unit 26 from second electrode 50b and third electrode 50c.

Figure 4:
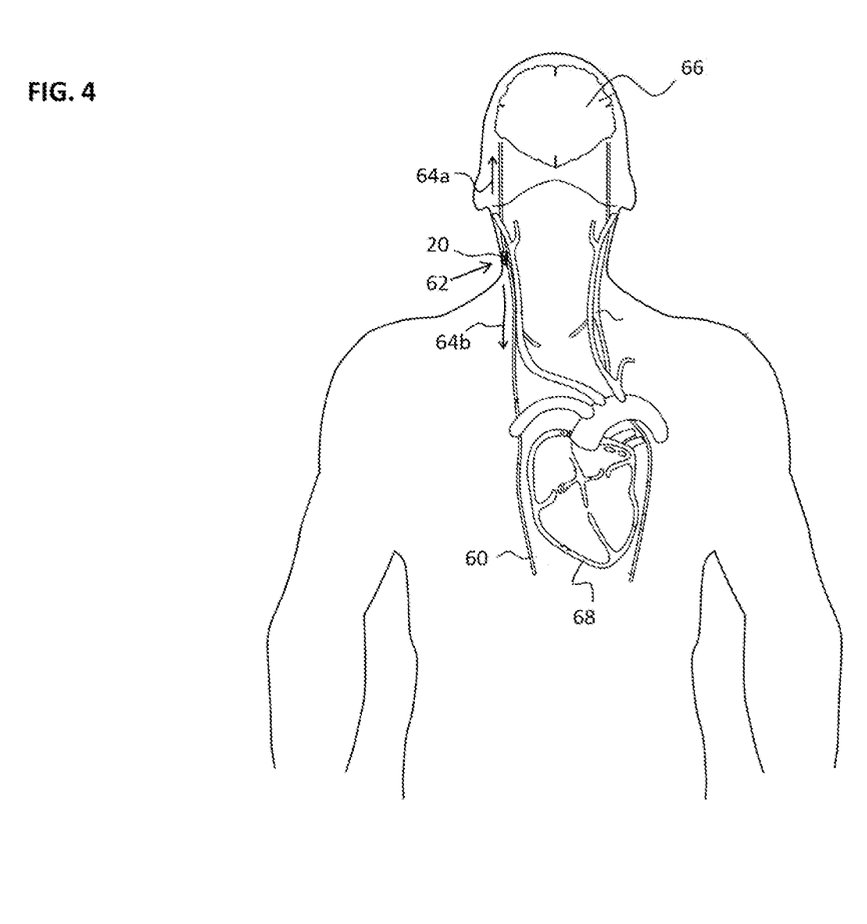
FIG. 4 is a schematic illustration of the apparatus implanted at a site on the vagus nerve of a subject, in accordance with some applications of the invention.
Figure 5:
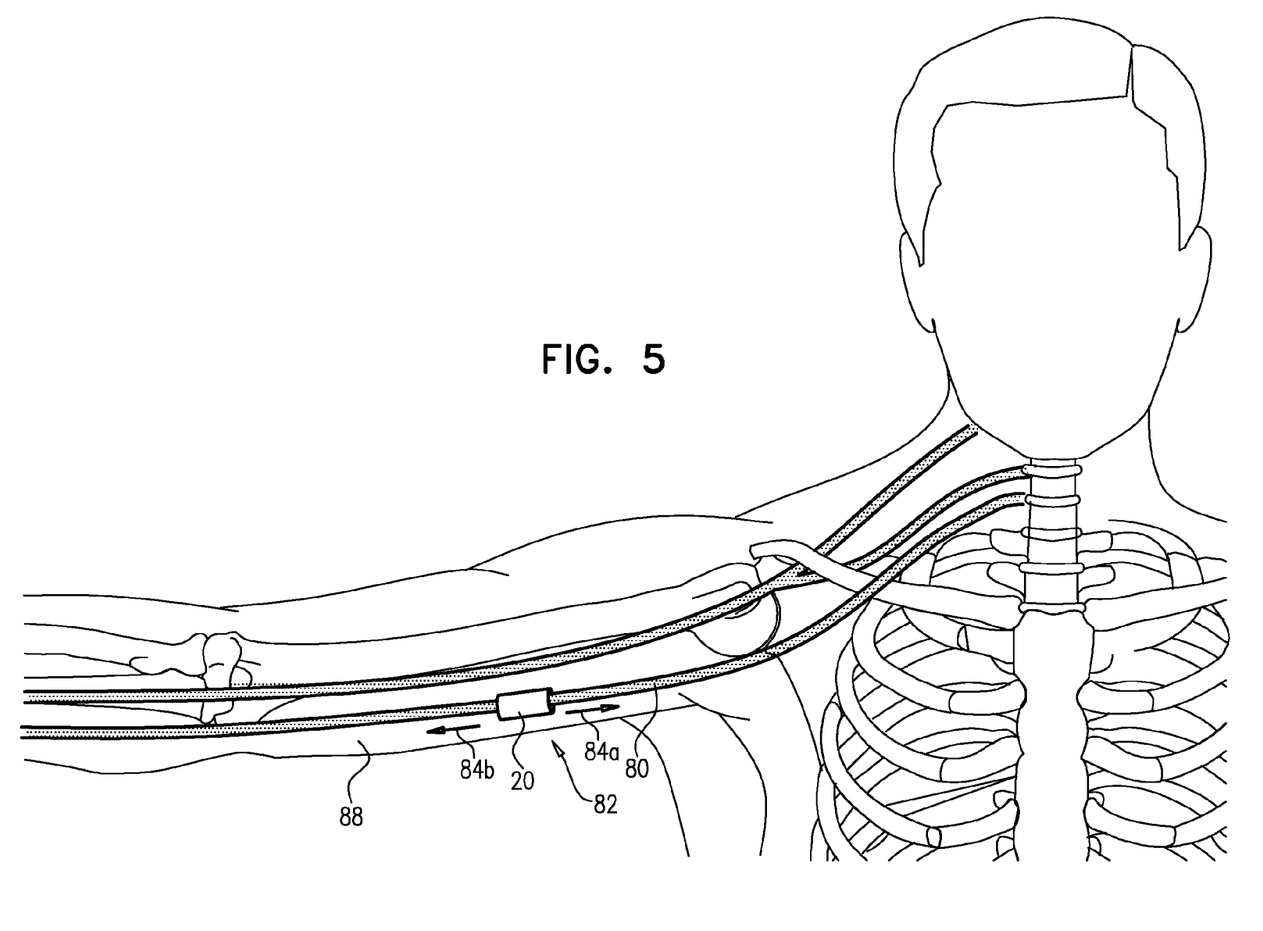
FIG. 5 is a schematic illustration of the apparatus implanted at a site on a nerve of a subject, in order to treat a tremor of the subject, in accordance with some applications of the invention.

Reference is made to FIGS. 4-5, which are schematic illustrations of non-limiting examples of implantation sites for apparatus 20, so as to have effects on two anatomical sites (e.g., to treat two conditions), in accordance with some applications of the invention.

Reference is now made to FIG. 4, which is a schematic illustration of apparatus 20, implanted at site 62 on the vagus nerve 60 of a subject who has been identified as suffering from epilepsy and heart failure, in accordance with some applications of the invention. As described, apparatus typically comprises a nerve cuff 22. The nerve cuff is placed around vagus nerve 60, typically such that electrodes of excitation units 24a and 24b, and blocking unit 26, are in electrical communication with the nerve.

Apparatus 20 initiates (1) one or more action potentials 64a, which propagate toward a site in the central nervous system (CNS), such as the brain 66 of the subject, and (2) one or more action potentials 64b, which propagate toward the heart 68 of the subject. Action potentials 64a and 64b are analogous to action potentials 24a and 24b, described hereinabove, respectively. Action potentials 64a are typically configured to treat epilepsy (e.g., using techniques described in U.S. Pat. No. 5,025,807 to Zabara, which is incorporated herein by reference). That is, apparatus 20 performs vagus nerve stimulation (VNS) such that epileptic seizures are reduced in frequency and/or intensity. Action potentials 64b are typically configured to treat heart failure (e.g., as described in U.S. Pat. No. 7,778,703 to Gross et al., which is incorporated herein by reference). That is, apparatus 20 performs VNS such that heart 68 is parasympathetically stimulated, typically reducing heart rate and/or blood pressure.

For some applications, apparatus 20 initiates action potentials according to a pre-defined program. For some applications, apparatus 20 initiates action potentials 64a in response to a detected parameter, e.g., a parameter indicative of an epileptic seizure. For some applications, apparatus 20 initiates action potentials 64b in response to a detected parameter, e.g., a parameter indicative of an episode of and/or deterioration in heart failure.

For some applications, apparatus 20 is used to treat epilepsy in subjects who are not identified as suffering from heart failure. As described hereinabove, apparatus 20 may be implanted in a first state and subsequently reconfigured to a second state. For example, apparatus 20 may be implanted in a subject that suffers from epilepsy, while the apparatus is in a first state configured to treat the epilepsy, in case the subject subsequently (e.g., years later) develops heart failure, at which time the apparatus may be reconfigured to additionally treat the heart failure, e.g., without requiring an additional invasive procedure.

Reference is now made to FIG. 5, which is a schematic illustration of apparatus 20, implanted at a site 82 on a nerve 80 of a subject who has been identified as suffering from tremor, in accordance with some applications of the invention. Typically, nerve 80 is a nerve that directly or indirectly innervates a skeletal muscle 88 of the subject (e.g., nerve 80 may be a mixed nerve). As described hereinabove, apparatus 20 typically comprises a nerve cuff 22. The nerve cuff is placed around nerve 80, such that electrodes of excitation units 24a and 24b, and blocking unit 26, are in electrical communication with the nerve. For some applications, and as shown in FIG. 5, nerve 80 comprises an ulnar nerve of the subject.

Action potentials 84a that propagate toward a site in the CNS, such as the spinal column 86 of the subject, and action potentials 84b that propagate toward a muscle 88, are initiated. Action potentials 84a and 84b are analogous to action potentials 24a and 24b, described hereinabove, respectively, and are configured to treat tremor.

Typically, apparatus 20 initiates action potentials 84a and/or 84b in response to a detected parameter, e.g., a parameter indicative of tremor, such as muscle stretching and/or action potentials in sensory neurons. For some applications, sensors 30 and/or 32 are configured to detect one or more factors indicative of tremor, and to responsively generate a signal indicative of tremor, and control unit 28 drives the excitatory current to initiate the generation of action potentials 84a and/or 84b in response to the signal. For example, sensor 30 may comprise an accelerometer, and be configured to generate the signal in response to detecting movement caused by the tremor. Alternatively or additionally, sensor 32 may be configured to detect tremor (e.g., sensor 32 may comprise a camera).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for stimulating a nerve of a subject, the apparatus being configured to drive first action potentials orthodromically in a first direction along the nerve, and second action potentials orthodromically along the nerve in an opposite direction to the first direction, the apparatus comprising:
    a first excitation unit and a second excitation unit, the excitation units being configured to be placed in a proximity of the nerve of the subject;
    a blocking unit disposed between the excitation units and configured to be placeable in a proximity of the nerve of the subject; and
    a control unit, configured:
        to drive the first excitation unit to apply a first excitatory current to the nerve of the subject,
        to drive the second excitation unit to apply a second excitatory current to the nerve of the subject, and
        to drive the blocking unit to apply a blocking current to the nerve of the subject that blocks action potentials that propagate from the first and second excitatory units toward the blocking unit.

2. The apparatus according to claim 1, wherein the control unit is configured to configure the blocking current to have a frequency of greater than 50 Hz.

3. The apparatus according to claim 1, wherein the blocking unit comprises at least one blocking electrode.

4. The apparatus according to claim 1, wherein the control unit is configured to apply the blocking current as a high frequency (HF) blocking current.

5. The apparatus according to claim 1, wherein:
    the apparatus comprises at least a first electrode, a second electrode, a third electrode, and a fourth electrode, and the control unit is configured:
        to define the first excitation unit from at least the first electrode and the second electrode,
        to define the second excitation unit from at least the third electrode and the fourth electrode, and
        to define the blocking unit from at least the second electrode and the third electrode.

6. The apparatus according to claim 1, wherein the control unit is configured to drive the first excitation unit to apply the first excitatory current independently from driving the second excitation unit to apply the second excitatory current.

7. The apparatus according to claim 6, wherein the control unit is configured to at least sometimes drive the first excitation unit to apply the first excitatory current at least 5 minutes away from a closest application of the second excitatory current by the second excitation unit.

8. The apparatus according to claim 6, wherein the control unit is configured to at least sometimes drive the first excitation unit to apply the first excitatory current at least 6 months away from a first application of the second excitatory current by the second excitation unit.

9. The apparatus according to claim 6, wherein the control unit is configurable to not drive the first excitation unit to apply the first excitatory current, and to subsequently be reconfigured to drive the first excitation unit to apply the first excitatory current.

10. The apparatus according to claim 1, further comprising a nerve cuff, wherein the excitation units and the blocking unit are disposed on the nerve cuff.

11. The apparatus according to claim 10, wherein:
    each excitation unit comprises at least one excitation electrode,
    the blocking unit comprises at least one blocking electrode,
    the nerve cuff is shaped to define a lumen, and has an inner surface, and
    the excitation electrodes and the blocking electrodes are disposed on the inner surface of the nerve cuff.

12. The apparatus according to claim 11, wherein the nerve cuff has two ends, and wherein each excitation unit is disposed closer to a respective one of the ends than is the blocking unit.

13. The apparatus according to claim 1, wherein each excitation unit comprises at least one electrode.

14. The apparatus according to claim 1, wherein the control unit is configured to:
    configure the first excitatory current to initiate propagation of first action potentials in the nerve of the subject,
    configure the second excitatory current to initiate propagation of second action potentials in the nerve of the subject,
    direct the first action potentials in a first direction along the nerve of the subject, and
    direct the second action potentials in a second direction along the nerve of the subject.

15. The apparatus according to claim 14, wherein the control unit is configured to direct the first action potentials in the first direction and the second action potentials in the second direction, by inhibiting propagation of the first action potentials in the second direction and propagation of the second action potentials in the first direction, by driving the blocking unit to apply the blocking current to the nerve of the subject.

16. The apparatus according to claim 14, wherein the control unit is configured to direct the first action potentials toward a site in a central nervous system of the subject.

17. The apparatus according to claim 14, wherein the control unit is configured to initiate the propagation of the first and second action potentials in the vagus nerve of the subject.

18. The apparatus according to claim 1, further comprising a sensor, configured to detect a factor indicative of a state of the subject, and wherein the control unit is configured to drive at least the first blocking unit to apply at least the first excitatory current in response to the detected factor.

19. The apparatus according to claim 18, wherein the sensor comprises an implantable sensor.

* * * * *